US008871227B2

(12) United States Patent
Haby et al.

(10) Patent No.: US 8,871,227 B2
(45) Date of Patent: Oct. 28, 2014

(54) PROCESS AND FORMULATION CONTAINING EPOTHILONES AND ANALOGS THEREOF

(75) Inventors: Thomas A. Haby, Hillsborough, NJ (US); Uday S. Gogate, North Brunswick, NJ (US); Vijay H. Naringrekar, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 420 days.

(21) Appl. No.: 12/557,822

(22) Filed: Sep. 11, 2009

(65) Prior Publication Data
US 2010/0016385 A1    Jan. 21, 2010

Related U.S. Application Data

(63) Continuation of application No. 10/979,958, filed on Nov. 3, 2004, now abandoned.

(60) Provisional application No. 60/517,020, filed on Nov. 4, 2003.

(51) Int. Cl.
*A61K 9/00* (2006.01)
*A01N 43/78* (2006.01)
*A61K 31/425* (2006.01)

(52) U.S. Cl.
CPC .................................. *A61K 31/425* (2013.01)
USPC .......................................... 424/400; 514/365

(58) Field of Classification Search
None
See application file for complete search history.

(56) References Cited

U.S. PATENT DOCUMENTS

| | | | |
|---|---|---|---|
| 6,210,938 B1 | 4/2001 | Barbas et al. | |
| 6,262,094 B1 | 7/2001 | Hoefle et al. | |
| 6,288,237 B1 | 9/2001 | Hoefle et al. | |
| 6,291,684 B1 | 9/2001 | Borzilleri et al. | |
| 6,294,374 B1 | 9/2001 | Sinha et al. | |
| 6,302,838 B1 | 10/2001 | O'Reilly et al. | |
| 6,303,342 B1 | 10/2001 | Julien et al. | |
| 6,309,881 B2 | 10/2001 | Barbas et al. | |
| 6,320,045 B1 | 11/2001 | Kim et al. | |
| 6,365,749 B1 | 4/2002 | Kim et al. | |
| 6,380,394 B1 | 4/2002 | Nicolaou et al. | |
| 6,380,395 B1 | 4/2002 | Vite et al. | |
| 6,387,927 B1 | 5/2002 | Altmann et al. | |
| 6,391,832 B2 * | 5/2002 | Lyons et al. | 508/491 |
| 6,410,301 B1 | 6/2002 | Julien et al. | |
| 6,441,186 B1 | 8/2002 | Nicolaou et al. | |
| 6,489,314 B1 | 12/2002 | Ashley et al. | |
| 6,495,534 B2 * | 12/2002 | Colombo et al. | 514/169 |
| 6,518,421 B1 | 2/2003 | Li et al. | |
| 6,531,497 B1 | 3/2003 | Nicolaou et al. | |
| 6,576,651 B2 | 6/2003 | Bandyopadhyay et al. | |
| 6,583,290 B1 | 6/2003 | Julien et al. | |
| 6,589,968 B2 | 7/2003 | Arslanian et al. | |
| 6,593,115 B2 | 7/2003 | Vite et al. | |
| 6,605,599 B1 | 8/2003 | Vite et al. | |
| 6,613,912 B2 | 9/2003 | Hoefle et al. | |
| 6,624,310 B1 | 9/2003 | Hoefle et al. | |
| 6,660,758 B1 | 12/2003 | Nicolaou et al. | |
| 6,670,384 B2 | 12/2003 | Bandyopadhyay et al. | |
| 6,683,100 B2 | 1/2004 | van Hoogevest | |
| 6,686,380 B2 | 2/2004 | Lee | |
| 6,689,802 B2 | 2/2004 | DiMarco et al. | |
| 6,727,276 B2 | 4/2004 | Lee | |
| 6,780,620 B1 | 8/2004 | Li et al. | |
| 6,800,653 B2 | 10/2004 | Kim et al. | |
| 2001/0034452 A1 | 10/2001 | Hoefle et al. | |
| 2002/0137152 A1 | 9/2002 | Santi et al. | |
| 2002/0143038 A1 | 10/2002 | Bandyopadhyay et al. | |
| 2003/0019877 A1 | 1/2003 | Scarabelli et al. | |
| 2003/0045711 A1 | 3/2003 | Ashley et al. | |
| 2003/0073677 A1 | 4/2003 | Lee | |
| 2003/0092478 A1 | 5/2003 | Weil | |
| 2003/0187039 A1 | 10/2003 | Favreau et al. | |
| 2003/0203876 A1 | 10/2003 | Hoogevest | |
| 2003/0203938 A1 | 10/2003 | Nicolaou et al. | |
| 2003/0220295 A1 | 11/2003 | Vite et al. | |
| 2003/0220378 A1 * | 11/2003 | Lee | 514/365 |
| 2004/0014982 A1 | 1/2004 | Hoefle et al. | |
| 2004/0023345 A1 | 2/2004 | Vite et al. | |
| 2004/0024032 A1 | 2/2004 | Voi et al. | |
| 2004/0049051 A1 | 3/2004 | Hoefle et al. | |
| 2004/0053978 A1 | 3/2004 | Lee et al. | |
| 2004/0072882 A1 | 4/2004 | Johnson, Jr. et al. | |
| 2004/0122081 A1 * | 6/2004 | Gogate et al. | 514/449 |
| 2004/0127432 A1 | 7/2004 | Nicolaou et al. | |
| 2004/0132146 A1 | 7/2004 | Benigni et al. | |
| 2004/0132754 A1 | 7/2004 | Brandt et al. | |
| 2004/0157897 A1 | 8/2004 | DiMarco et al. | |
| 2004/0214871 A1 | 10/2004 | Lee | |
| 2004/0235796 A1 | 11/2004 | Chen et al. | |
| 2004/0253697 A1 | 12/2004 | Julien et al. | |
| 2006/0013836 A1 * | 1/2006 | Bandyopadhyay et al. | 424/400 |

FOREIGN PATENT DOCUMENTS

| | | | |
|---|---|---|---|
| DE | 4138042 | | 5/1993 |
| WO | WO 98/22461 | | 5/1998 |
| WO | WO 0037473 | * | 6/2000 |
| WO | WO 03/018002 | | 3/2003 |
| WO | WO 03/049734 | | 6/2003 |
| WO | WO 03/057217 | | 7/2003 |

OTHER PUBLICATIONS

U.S. Appl. No. 10/805,724, filed Mar. 22, 2004, Benigni et al.

* cited by examiner

*Primary Examiner* — Snigdha Maewall
(74) *Attorney, Agent, or Firm* — Burton Rodney

(57) ABSTRACT

A process for formulating certain epothilones and analogs thereof for parenteral administration is provided wherein the pH of the formulation for administration can be controlled to enhance the stability and thus, potency of the epothilone, or analog thereof.

8 Claims, No Drawings

PROCESS AND FORMULATION CONTAINING EPOTHILONES AND ANALOGS THEREOF

CROSS-REFERENCE TO RELATED APPLICATIONS

This application is a continuation of U.S. application Ser. No. 10/979,958, filed Nov. 3, 2004 which claims the priority benefit of U.S. Provisional Application No. 60/517,020, filed Nov. 4, 2003, incorporated herein by reference in their entirety.

FIELD OF THE INVENTION

The present invention relates to a process and formulation for preparing certain epothilones and analogs thereof for administration to patients, in which there is achieved enhanced control of infusion pH, leading to increased infusion stability.

BACKGROUND OF THE INVENTION

Epothilones are macrolide compounds having utility in the pharmaceutical field. For example, Epothilones A and B are naturally-occurring compounds that can be isolated from certain microorganisms, having the structures:

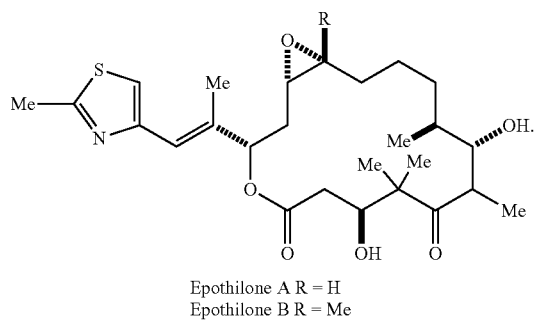

Epothilone A R = H
Epothilone B R = Me

Known epothilones exert microtubule-stabilizing effects similar to TAXOL® and therefore exhibit cytotoxic activity against rapidly proliferating cells, such as occur in cancer and other hyperproliferative cellular diseases (See *Angew. Chem. Int. Ed. Engl.*, Vol. 35, No. 13/14, 1996 and D. M. Bollag, *Exp. Opin. Invest. Drugs*, 6(7): 867-873, 1997).

Since the introduction of epothilones into the art, many groups have been designing, synthesizing and testing analogs of the naturally occurring epothilones in an attempt to develop useful pharmaceuticals. (See, e.g., D. Schinzer et al. *Angew. Chem. Int. Ed. Eng.*, 1997, 36, No. 3, 523-524; K. C. Nicolaou, et al., *J. Amer. Chem. Soc.*, 1997, 119, 7974-7991; (K. C. Nicolaou et al., *Angew. Chem. Int. Ed. Engl.*, 1996, 35, No. 20, 2399-2401; A. Balog et al., *Angew. Chem. Int. Ed. Engl.*, 1996, 35, No. 23/24, 2801-2803).

Before epothilones can be used to treat diseases in patients, however, they must be formulated into a pharmaceutical composition that can be administered to the patient; for example, into a dosage form suitable for oral, mucosal (e.g., nasal, sublingual, vaginal, buccal, or rectal), parenteral (e.g., subcutaneous, intravenous, bolus injection, intramuscular, or intraarterial), or transdermal administration.

Certain epothilones and analogs thereof having advantageous activity are represented by formula I:

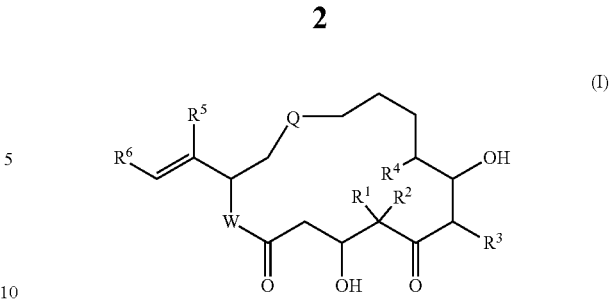

wherein the various symbols are as defined below. These and other epothilone analogs are further described, for example, in U.S. Pat. Nos. 6,605,599, 6,262,094, 6,288,237 B1, 6,613,912, and U.S. patent application Ser. Nos. 09/836,134 and 10/602,770, each of which is assigned to the present assignee and incorporated herein by reference in its entirety.

While these and other epothilone analogs possess significant therapeutic properties, they also present challenges to those skilled in the art of pharmaceutical compounding as a result of certain chemical properties. For example, certain epothilones and/or analogs thereof are susceptible to acid-catalyzed hydrolysis and thus, can rapidly degrade at low pH. In accordance with the present invention, a process and formulation have been found whereby epothilones and analogs thereof can be administered to a patient while achieving enhanced pH control of the formulation and thus, enhanced stability of the epothilones and analogs thereof. In one embodiment, the invention comprises a formulation for intravenous injection using cost-effective and readily-available infusion fluids such as saline and/or dextrose. Other formulations for administration of epothilones and epothilone analogs are described in U.S. patent application Ser. No. 10/051,727 filed Jan. 17, 2002, 10/055,653, filed Jan. 23, 2002, and Ser. No. 10/404,324, filed Apr. 1, 2003, each of which is assigned to the present assignee, and each of which is incorporated herein by reference in its entirety.

SUMMARY OF THE INVENTION

The present invention describes a pharmaceutical preparation comprising epothilones and analogs thereof, of formula I:

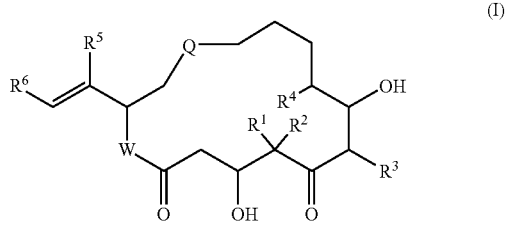

wherein the various symbols are as defined below. According to one aspect of the invention, there is provided a process of formulating at least one epothilone or analog thereof for administration to a patient, said process comprising dissolving the epothilone, or analog thereof with a solution vehicle which includes at least one buffer and a pH-adjusting ingredient, to define an epothilone solution. The epothilone solution is then further diluted in an infusion fluid to provide a formulation for administration, wherein the pH of the formulation for administration is controlled by the buffer and pH-adjusting ingredient in the first solution vehicle. According to one aspect of the invention, an epothilone analog is lyophilized, and then the lyophilized epothilone analog is dissolved in solution vehicle (in this embodiment, the solution vehicle defines a vehicle for reconstitution of the lyophilized epothilone analog) to provide an epothilone solution, wherein the solution vehicle includes a surfactant, dehydrated alcohol a buffer, and a base, and then the epothilone solution is diluted with an infusion fluid to a concentration appropriate for a formulation for administration, thereby achieving a formulation that can be administered without appreciable loss of potency.

DETAILED DESCRIPTION OF THE INVENTION

Definitions

The following are definitions of various terms used herein to describe the present invention. These definitions apply to the terms as they are used throughout this specification, unless otherwise limited in specific instances, either individually or as part of a larger group.

When reference herein is made to epothilones and analogs thereof represented by formula I:

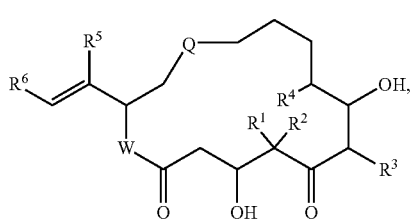

(I)

it is meant that the groups designated as W, Q, $R^1$, $R^2$, $R^3$, $R^4$, and $R^5$, shall unless otherwise designated have the following meanings:

Q is selected from the group consisting of:

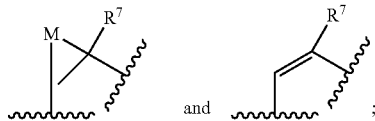

and ;

W is selected from —O— and —N($R^{16}$)—;

M is selected from the group consisting of oxygen, sulfur, —N($R^8$)—, and —C($R^9R^{10}$)—;

each $R^1$, $R^2$, $R^3$, $R^4$, $R^5$, and $R^7$ is, independently, selected from the group consisting of hydrogen, alkyl, substituted alkyl, aryl, substituted aryl, and heterocyclo, and wherein when $R^1$ and $R^2$ are alkyl, they can be joined to form cycloalkyl;

$R^6$ is selected from the group consisting of hydrogen, alkyl, substituted alkyl, aryl, substituted aryl, cycloalkyl, heterocyclo, and substituted heterocyclo;

$R^8$ is selected from the group consisting of hydrogen, alkyl, substituted alkyl, —C(=O)$R^{11}$, —C(=O)O$R^{12}$, and —S($O_2$)$R^{13}$;

$R^9$ and $R^{10}$ are each independently selected from the group consisting of hydrogen, halogen, alkyl, substituted alkyl, aryl, heterocyclo, hydroxy, —C(=O)$R^{14}$, and —C(=O)O$R^{15}$; and each $R^{11}$, $R^{12}$, $R^{13}$, $R^{14}$, $R^{15}$, and $R^{16}$ is, independently, selected from the group consisting of hydrogen, alkyl, substituted alkyl, aryl, substituted aryl, and heterocycle.

The term "alkyl" refers to optionally substituted straight- or branched-chain saturated hydrocarbon groups having from 1 to about 20 carbon atoms, preferably from 1 to about 7 carbon atoms. The expression "lower alkyl" refers to alkyl groups having from 1 to 4 carbon atoms. A "substituted lower alkyl" refers to an alkyl group having from 1 to 4 carbon atoms and one, two, or three (preferably one or two) substituents selected from those recited for "substituted alkyl" groups.

The term "substituted alkyl" refers to an alkyl group substituted by, for example, one to four substituents (preferably one to two substituents), such as, halo, trifluoromethyl, trifluoromethoxy, hydroxy, alkoxy, cycloalkyoxy, heterocyclooxy, oxo (=O), alkanoyl, aryl, aryloxy, aralkyl, alkanoyloxy, amino, alkylamino, arylamino, aralkylamino, cycloalkylamino, heterocycloamino, disubstituted amino (in which the two substituents on the amino group are selected from alkyl, aryl, and/or aralkyl), alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g., $SO_2NH_2$), substituted sulfonamido, nitro, cyano, carboxy, carbamyl (e.g., $CONH_2$), substituted carbamyl (e.g., CONRR', wherein R and R' are selected from hydrogen, alkyl, and/or aryl, provided at least one of R and R' is other than hydrogen), alkoxycarbonyl, aryl, substituted aryl, guanidino and heterocyclo, such as indolyl, imidazolyl, furyl, thienyl, thiazolyl, pyrrolidyl, pyridyl, pyrimidyl, and the like. Wherein, as noted above, the substituents themselves are further substituted, such further substituents are selected from the group consisting of halogen, alkyl, alkoxy, aryl and aralkyl. The definitions given herein for alkyl and substituted alkyl apply as well to the alkyl portion of alkoxy groups.

The term "halogen" or "halo" refers to fluorine, chlorine, bromine, and iodine.

The term "aryl" refers to monocyclic or bicyclic aromatic hydrocarbon groups having from about 6 to about 12 carbon atoms in the ring portion, for example, phenyl, and naphthyl.

The term "aralkyl" refers to an aryl group bonded to a larger entity through an alkyl group, for example, a benzyl group.

The term "substituted aryl" refers to an aryl group substituted by, for example, one to four substituents (preferably one to two substituents) such as alkyl, substituted alkyl, halo, trifluoromethyl, trifluoromethoxy, hydroxy, alkoxy, cycloalkyloxy, heterocyclooxy, alkanoyl, alkanoyloxy, amino, alkylamino, dialkylamino, aralkylamino, cycloalkylamino, heterocycloamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonanido, aryloxy, and the like. The substituent may be further substituted by one or more members selected from the group consisting of halo, hydroxy, alkyl, alkoxy, aryl, substituted alkyl, substituted aryl, and aralkyl.

The term "cycloalkyl" refers to optionally substituted saturated cyclic hydrocarbon ring systems, preferably containing 1 to 3 rings and 3 to 7 carbons per ring, which may be further fused with an unsaturated $C_3$-$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl or substituted alkyl groups as described above, or one or more of the groups described above as substituents for alkyl groups. Additionally, a cycloalkyl may contain a carbon-carbon bridge of one to two bridgehead carbon atoms, and/or one or two (preferably one) of the ring carbon atoms optionally may be replaced with a carbonyl group (substituted with keto).

The terms "heterocycle", "heterocyclic" and "heterocyclo" refer to an optionally substituted, unsaturated, partially saturated, or fully saturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2, or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, and tetrahydro-1,1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzothiazolyl, benzopyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, indolyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Smaller heterocyclos, such as, epoxides, aziridines, and the like, are also included.

Exemplary substituents for the groups "heterocycle," "heterocyclic," and "heterocyclo" include alkyl, substituted alkyl, or one or more substituent groups as described above for substituted alkyl or substituted aryl groups.

The term "alkanoyl" refers to C(O)-alkyl.

The term "substituted alkanoyl" refers to —C(O)-substituted alkyl.

The term "heteroatoms" shall include oxygen, sulfur, and nitrogen.

The term "pH-adjusting ingredient" denotes an acid, base, or mixtures thereof (preferably a base, such as sodium hydroxide, potassium hydroxide, lithium hydroxide), which is selected to adjust the pH of the infusion fluid that is used for delivery of the epothilones and analogs thereof. According to one aspect of the invention, the pH-adjusting ingredient is preferably selected in amount and type sufficient to achieve, for the formulation for administration, a pH that approximates the epothilone or epothilone analog's pH of maximum stability.

The term "low pH" as used herein means a pH below 7, more preferably a pH below 6.

The term "pH differential" as used herein refers to the difference between (a) the pH of maximum stability for the epothilone or analog thereof to be administered to a patient, and (b) the pH of the infusion fluid selected to be used to administer the epothilone, or analog thereof, to a patient.

The term, "pH of maximum stability," or "maximum stability pH" means the pH at which a compound (or mixture of compounds) is least likely to degrade, or at which the compound (or mixtures of compounds) will degrade most slowly. Each compound or mixture of compounds will have a pH of maximum stability. However, the pH of maximum stability also may encompass a range of pH's. For example, it may be determined that a compound is equally stable at the pH of 7 and 7.2, but less stable at pH 6.9. In this case, the pH of maximum stability is 7.1±1.

The terms "diluent" and "infusion fluid" are used interchangeably herein to denote the fluid for administration to a patient, such as via parenteral (e.g., subcutaneous, intravenous, bolus injection, intramuscular, or intraarterial) administration.

When it is stated herein that a formulation is provided having enhanced stability, the term "enhanced stability" is intended to mean that the epothilones, or analogs thereof, included in the formulation will degrade less rapidly as compared with the same epothilones, or analogs thereof, included in a formulation having the same ingredients except without the buffer and pH-adjusting ingredient included. Preferably, the formulation according to the invention will have an enhanced stability of about 25% or greater determined over a period of up to 24 hours (in the range of 0 to 24 hours).

The compounds represented by formula I form salts with a variety of organic and inorganic acids. Such salts include those formed with hydrogen chloride, hydrogen bromide, methanesulfonic acid, hydroxyethanesulfonic acid, sulfuric acid, acetic acid, trifluoroacetic acid, maleic acid, benzenesulfonic acid, toluenesulfonic acid and various others as are recognized by those of ordinary skill in the art of pharmaceutical compounding. Such salts are formed by reacting a compound represented by formula I in an equivalent amount of the acid in a medium in which the salt precipitates or in an aqueous medium followed by evaporation.

In addition, zwitterions ("inner salts") can be formed and are included within the term salts as used herein.

The present invention also provides a process for the formulation of an epothilone analog of formula I. The present invention further provides a process for preparing a pharmaceutical preparation for parenteral administration.

Preferred Epothilone Analogs

Preferred epothilone analogs of formula I, advantageous for use in the present invention include compounds of formula (I*),

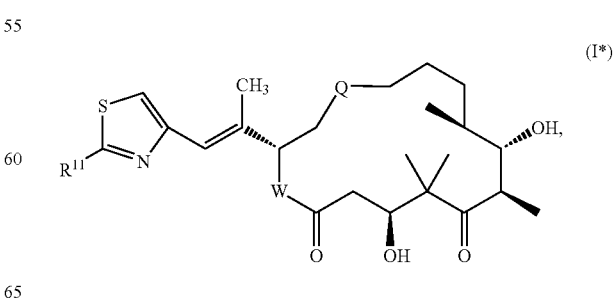

and pharmaceutically acceptable salts and solvates thereof, wherein,

Q is selected from the group consisting of:

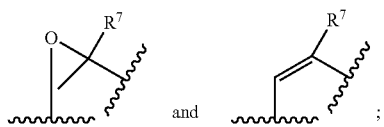

W is —O— or NH—;

$R^7$ is hydrogen or lower alkyl (more preferably methyl); and $R^{11}$ is selected from lower alkyl (more preferably methyl), optionally substituted with hydroxy, lower alkoxy, amino, or $C_{1-4}$alkylamino (more preferably hydroxy or amino, even more preferably amino).

A particularly preferred example of an epothilone analog of formula I is [1S-[1R*,3R*(E),7R*,10S*,11R*,12R*, 16S*]]7,11-Dihydroxy-8,8,10,12,16-pentamethyl-3-[1-methyl-2-(2-methyl-4-thiazolyl)ethenyl]-4-aza-7oxabicyclo[14.1.0]heptadecane-5,9-dione (represented by formula II):

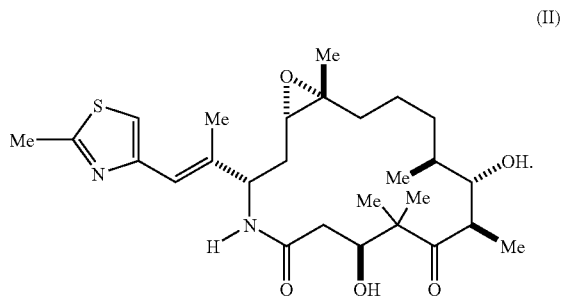

(II)

The compounds represented by formulae I and II and processes for their preparation are described in U.S. Pat. No. 6,605,599, and international patent application WO99/02514 published Jan. 21, 1999 (both assigned to the present assignee), as well as U.S. Pat. No. 6,518,421, U.S. Pat. No. 6,262,094, the disclosures of each of which are incorporated herein by reference. The compounds represented by formulae I and II may exist as multiple optical, geometric, and stereoisomers. While the compounds shown herein are depicted for one optical orientation, included within the present invention are all isomers and mixtures thereof.

Utility

Compounds represented by formulae I and II are microtubule-stabilizing agents. They are thus useful in the treatment of a variety of cancers and other proliferative diseases including, but not limited to, the following:

carcinoma, including that of the bladder, breast, colon, kidney, liver, lung, ovary, pancreas, stomach, cervix, thyroid, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, and Burketts lymphoma;

hematopoietic tumors of myeloid lineage, including acute and chronic myelogenous leukemias and promyelocytic leukemia;

tumors of mesenchymal origin, including fibrosarcoma and rhabdomyoscarcoma;

other tumors, including melanoma, seminoma, teratocarcinoma, neuroblastoma, and glioma;

tumors of the central and peripheral nervous system, including astrocytoma, neuroblastoma, glioma, and schwannomas;

tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer, and teratocarcinoma.

Compounds represented by formulae I and II will also inhibit angiogenesis, thereby affecting the growth of tumors and providing treatment of tumors and tumor-related disorders. Such anti-angiogenesis properties will also be useful in the treatment of other conditions responsive to anti-angiogenic agents including, but not limited to, certain forms of blindness related to retinal vascularization, arthritis, especially inflammatory arthritis, multiple sclerosis, restenosis, and psoriasis.

Compounds represented by formulae I and II will induce or inhibit apoptosis, a physiological cell death process critical for normal development and homeostasis. Alterations of apoptotic pathways contribute to the pathogenesis of a variety of human diseases. Compounds represented by formula I and II, as modulators of apoptosis, will be useful in the treatment of a variety of human diseases with aberrations in apoptosis including, but not limited to, cancer and precancerous lesions, immune response related diseases, viral infections, kidney disease, and degenerative diseases of the musculoskeletal system.

Compounds represented by formulae I and II may also be formulated or co-administered with other therapeutic agents that are selected for their particular usefulness in administering therapies associated with the aforementioned conditions. For example, methods for administering compounds of formula I and II are described in U.S. patent application Ser. No. 10/091,061, filed Mar. 5, 2002, incorporated herein by reference in its entirety. Compounds of formulae I and II may be formulated with agents to prevent nausea, hypersensitivity, and gastric irritation, such as anti-emetics, and $H_1$ and $H_2$ antihistamines. The above therapeutic agents, when employed in combination with a compound of formulae I or II, may be used in those amounts indicated in the Physicians' Desk Reference (PDR) or as otherwise determined by one of ordinary skill in the art.

Furthermore, compounds represented by formulae I and II may be administered in combination with other anti-cancer and cytotoxic agents and treatments useful in the treatment of cancer or other proliferative diseases. Especially useful are anti-cancer and cytotoxic drug combinations wherein the second drug chosen acts in a different manner or different phase of the cell cycle, e.g., S phase, than the present compounds of formulae I and II which exert their effects at the $G_2$-M phase. Examples of classes of anti-cancer and cytotoxic agents include, but are not limited to, alkylating agents, such as nitrogen mustards, alkyl sulfonates, nitrosoureas, ethylenimines, and triazenes; antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone anatagonists, octreotide acetate; microtubule-disruptor agents, such as ecteinascidins or their analogs and derivatives; microtubule-stabilizing agents such as paclitaxel (TAXOL®), docetaxel (TAXOTERE®); plantderived products, such as vinca alkaloids, epipodophyllotoxins, and taxanes; topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin; and other agents used as anti-cancer and cytotoxic agents such as biological response modifiers, growth factors, immune modulators, and monoclonal antibodies. Compounds represented by formulae I and II may also be used in conjunction with radiation therapy.

Representative examples of these classes of anti-cancer and cytotoxic agents include, but are not limited to, mechlorethamine hydrochlordie, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin (including salts such as doxorubicin hydrochloride), daunorabicin, idarubicin, bleomycin sulfate, mitomycin C, actinomycin D, safracins, saframycins, quinocarcins, discodermolides, vincristine, vinblastine, vinorelbine tartrate, etoposide (including salts such as etoposide phosphate), teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, capecitabine, gemcitabine hydrochloride, altretamine, and topoteca and analogs or derivatives thereof.

Other examples of these classes of anticancer and cytotoxic agents include, but are not limited to, cisplatin, carboplatin, caminomycin, aminopterin, methotrexate, methopterin, ecteinascidin 743, porfiromycin, 5-fluorouracil (5-FU), 6-mercaptopurine, gemcitabine, cytosine arabinoside, podophyllotoxin or podophyllotoxin derivatives, leurosidine, vindesine, and leurosine. It is to be understood the compounds of formulae I and II may be administered in combination with particular anticancer and cytotoxic agents falling within these classes of agents, for example, the compounds of formulae I and II may be administered in combination with any 5-FU agents, and/or prodrugs thereof, including without limitation capecitabine (XELODA®).

Further examples of anti-cancer and other cytotoxic agents include the following: cyclin dependent kinase inhibitors as found in WO 99/24416; and prenyl-protein transferase inhibitors as found in WO 97/30992 and WO 98/54966.

Without being bound by any theory regarding mechanism or morphology, the compounds represented by formulae I and II may also be used to treat conditions other than cancer or other proliferative diseases Such conditions include, but are not limited to viral infections such as herpesvirus, poxvirus, Epstein-Barr virus, Sindbis virus and adenovirus; autoimmune diseases such as systemic lupus erythematosus, immune mediated glomerulonephritis, rheumatoid arthritis, psoriasis, inflammatory bowel diseases, and autoimmune diabetes mellitus; neurodegenerative disorders such as Alzheimer's disease, AIDS-related dementia, Parkinson's disease, amyotrophic lateral sclerosis, retinitis pigmentosa, spinal muscular atrophy, and cerebellar degeneration; AIDS; myelodysplastic syndromes; aplastic anemia; ischemic injury associated myocardial infarctions; stroke and reperfusion injury; restenosis; arrhythmia; atherosclerosis; toxin-induced or alcohol induced liver diseases; hematological diseases such as chronic anemia and aplastic anemia; degenerative diseases of the musculoskeletal system such as osteoporosis and arthritis; aspirin-sensitive rhinosinusitis; cystic fibrosis; multiple sclerosis; kidney diseases; and pain, particularly cancer pain.

The effective amount of a compound represented by formulae I and II may be determined by one of ordinary skill in the art. Exemplary dosage amounts may be found in U.S. patent application Ser. No. 10/055,653, filed Jan. 23, 2002, incorporated herein by reference. Alternatively, for a human of from about 0.05 mg/kg/day to about 200 mg/kg/day, compounds of formula I and II may be administered in a single dose or in the form of individual divided doses, such as from 1 to about 4 times per day. For example, the compounds used in the present invention may be administered in a dosage of less than about 100 mg/kg/day, in a single dose or in about 2 to about 4 divided doses. It will be understood that the specific dose level and frequency of dosage for any particular subject may be varied and will depend upon a variety of factors including the activity of the specific compound employed, the metabolic stability and length of action of that compound, the species, age, body weight, general health, sex, and diet of the subject, the mode and time of administration, rate of excretion, drug combination, and severity of the particular condition. Subjects for treatment include animals, including species such as humans, and domestic animals such as dogs, cats and the like, subject to the aforementioned disorders.

Description of Process and Formulation

The compounds represented by formulae I and II present challenges from the viewpoint of pharmaceutical compounding for administration to patients for a number of reasons. For example, compounds of formula I and II present a number of solubility and stability issues, e.g., they possess low solubility and can degrade when in contact with aqueous media and/or when exposed to light. Of particular concern with the present invention, compounds of formulae I and II can degrade when exposed to low pH, e.g., certain compounds of formula I presumably are susceptible to acids catalyzed hydrolysis. For example, the time for 5% drug loss ($t_{95}$) at 25° for an aqueous solution of compound II is approximately 2 h at pH 7, but less than 0.2 h at pH 2.5.

This pH sensitivity presents drawbacks in that a number of readily-available, commonly-used, and cost-effective infusion fluids (such as saline and dextrose) exhibit low pH. In particular, the infusion fluids (or diluents) comprising 0.9% Sodium Chloride Injection (USP) have a relatively low pH ranging from a pH of 4.5 to 7.0, and diluents comprising 5% Dextrose Injection (USP) have a pH of 3.5 to 6.5, and therefore, may lead to instability of the epothilone formulations.

One alternative to address these drawbacks relating to the pH sensitivity of the epothilones and analogs thereof, is to use an alternative diluent, having a higher pH. For example, U.S. patent application Ser. No. 10/055,653, filed Jan. 23, 2002, states that because of its narrow pH range, Lactated Ringer's Injection (LRI) is preferred as a diluent in that formulation. Per 100 mL, Lactated Ringer's Injection contains Sodium Chloride USP 0.6 g, Sodium Lactate 0.31 g, Potassium chloride USP 0.03 g and Calcium Chloride.2H$_2$O USP 0.02 g. The osmolarity is 275 mOsmol/L, which is very close to isotonicity, and it has a pH of 6.0 to 7.5. However, LRI may not be as widely-available as saline or dextrose infusion fluids, and it is more expensive. If the pH drawbacks associated with saline and dextrose could be overcome, these infusion fluids would be advantageous, as they are readily available world-wide, are commonly-used, and are less expensive than some other infusion fluids, such as LRI.

Applicants have found a novel process and preparation that enables use of such infusion fluids having low pH, wherein the epothilones and analogs thereof have enhanced stability as compared with previous formulations including the use of such infusion fluids. According to one aspect of the invention, the epothilone, or analog thereof, is dissolved in a first, solution vehicle to provide an epothilone solution, wherein the solution vehicle includes (in addition to solvent) at least one buffer and at least one pH-adjusting ingredient, e.g., a base, and then the epothilone solution is mixed with an infusion fluid to provide a formulation for administration. The selection and concentration of the buffer is determined as a function of the dose of epothilone, or analog thereof. The solution vehicle is advantageously prepared to achieve a pH for the epothilone solution whereby, when the epothilone solution is mixed with the infusion fluid, the pH of the formulation for administration is approximately equal to the pH of maximum stability of the epothilone, or analog thereof.

For example, in the embodiment involving use of the epothilone analog of formula II, the pH of maximum stability is about 7.0. A preferred dose of this epothilone analog when diluted in the infusion fluid is approximately in the range of about 0.05 to about 1.0 mg/mL, more preferably in the range of about 0.1 to about 0.8 mg/mL, and most preferably in the range of about 0.2 to about 0.6 mg/mL. The inventors herein have determined that for this epothilone analog and preferred dose, an advantageous buffer is sodium lactate, and a preferred concentration of this buffer in the formulation for administration is in the range of about 3 to about 30 mg/mL, more preferably in the range of about 10 to about 20 mg/mL, even more preferably at a concentration of about 15 mg/mL. To achieve this concentration of buffer in the formulation for administration, an advantageous concentration of sodium lactate solution (60% sodium lactate) buffer in the solution is about 20 to 30 mg/mL, more preferably about 25 mg/mL. Using this concentration of buffer, the solution vehicle is then preferably prepared (e.g., using the type and amount of base selected for this objective) to achieve a pH in the range of about 6 to about 9, more preferably in the range 8.0 to 8.8, even more preferably in the range 8.2 to 8.6, and most preferably at 8.4±0.1. To achieve this pH, for example, using 1N or 2N Sodium Hydroxide Solution, the final concentration of sodium hydroxide in the solution vehicle advantageously ranges from about 0.01 mg/mL to about 1 mg/mL. When the solution vehicle containing dissolved epothilone, having the desired pH for said solution vehicle, is then mixed with the infusion fluid, e.g., wherein the infusion fluid advantageously includes saline or dextrose, the pH of the formulation for administration is advantageously in the range of 6.0 to 10.0, more preferably in the range 7.0 to 9.0.

According to the invention, the pH of the solution vehicle can be adjusted (e.g., by choice and concentration of buffer and base) to control the pH of the formulation for administration, depending upon the selection and dose of the particular epothilone or analog thereof, the choice and concentration of buffer, and the composition or components of the infusion fluid. Applying these concepts, the invention may be carried out in a number of ways. For example, the solution vehicle may be prepared by mixing sodium lactate with an anhydrous alcohol, such as Dehydrated Alcohol followed by the addition of sodium hydroxide (1N or 2N solution) and CREMOPHOR EL® brand of polyethoxylated castor oil surfactant. Alternatively, the solution vehicle can be prepared by mixing sodium lactate with an anhydrous alcohol, such as Dehydrated Alcohol and CREMOPHOR EL® brand of polyethoxylated castor oil surfactant followed by the addition of sufficient sodium hydroxide solution (2N).

As may be appreciated from the foregoing, the inventors herein have discovered a preparation including use of a buffer and base, wherein when the preparation is added to the epothilone, or analog thereof, dissolved in solution, the pH of the subsequent formulation for administration, i.e., prepared upon addition of the infusion fluid, can be controlled in the range of 6.0 to 10, for example, 6.5 to 7.5. In other words, with the inventive preparation, the pH differential between the infusion fluid pH, and the pH of maximum stability for the compound being administered, can be reduced. The ability to control the formulation pH thus provides for a formulation for administration wherein the epothilones or analogs thereof have enhanced stability and thus, increased potency, as compared with the same formulation without buffer and base included.

To illustrate the surprising advantages of the invention, a formulation including the compound of formula II was diluted in a 0.9% Sodium Chloride Injection infusion fluid to a concentration of 0.2 mg/mL, without buffer and base. Over a six hour hold time, this formulation demonstrated a loss of potency (degradation in active compound) of about 6%. However, when the present invention was applied with the same formulation but including the use of buffer and base, the loss of potency (degradation of active compound) over the six hour hold time was about 3.6%, representing an approximately 40% enhancement in stability. As a further illustration, a formulation including the compound of formula II was diluted in a 5% dextrose injection fluid to a concentration of 0.2 mg/mL, without buffer and base. Over a six hour hold time, this formulation demonstrated a loss of potency (degradation in active compound) of about 13%. However, when the present invention was applied with the same formulation but including the use of buffer and base, the loss of potency (degradation of active compound) over the six hour hold time was about 4%, representing an enhancement of stability of greater than 65%.

In preparing the solution vehicle, the preferred buffer is sodium lactate, more preferably 60% Sodium Lactate, USP, and a preferred base is sodium hydroxide, more preferably added to the solution as 1N or 2N sodium hydroxide solutions. However, other buffers and bases may be used as determined by one skilled in the field. Exemplary buffers that may be used include, but are not limited to sodium phosphate, sodium citrate, L-lysine, L-histidine, L-alanine, and tris-hydroxymethyl aminomethane. Exemplary bases include, but are not limited to platinum oxide ($PtO_2$), potassium hydroxide (KOH), sodium hydroxide (NaOH), lithium hydroxide (LiOH), potassium carbonate ($K_2CO_3$), sodium bicarbonate ($NaHCO_3$), magnesium hydroxide ($Mg(OH)_2$), and Calcium Hydroxide ($Ca(OH)_2$).

Additionally, the solution vehicle used to dissolve the epothilones, or analogs thereof, in addition to buffer and base, will naturally include one or more solvents and advantageously one or more surfactants. One skilled in the field can select appropriate solvents and surfactants for use with the invention. For example, various solvents and surfactants are described in U.S. patent application Ser. No. 10/051,727 filed Jan. 17, 2002, Ser. No. 10/055,653, filed Jan. 23, 2002, and Ser. No. 10/404,324, filed Apr. 1, 2003, each of which is assigned to the present assignee and incorporated herein by reference in its entirety. A preferred solvent for the solution vehicle is a Dehydrated Alcohol USP, and a preferred surfactant is a nonionic surfactant, such as a polyethoxylated castor oil surfactant. More preferably the solvent/surfactant system includes Ethanol and CREMOPHOR EL® brand of polyethoxylated castor oil surfactant (available from GAF Corp., Mount Olive, N.J., under the tradename CREMOPHOR EL®), more preferably in 1:1 amounts thereof.

Advantageously, the epothilones or analogs thereof are lyophilized prior to being dissolved in the solution vehicle. In this embodiment, the solution vehicle may be considered a reconstitution vehicle for reconstituting the lyophilized epothilones into a liquid form. Techniques and processes for lyophilization are set forth in U.S. patent application Ser. Nos. 10/051,727 and 10/055,653, incorporated herein and further referenced above. More particularly, in one embodiment, the epothilones or analogs thereof can be first placed into a solution involving a mixture of tertiary-butanol and water for injection and then lyophilized from this solution. This mixture is preferably about 50% v/v, for example, from about 50% to about 80% v/v tertiary butanol to reduce degradation of the subject epothilones and analogs thereof. Due to poor wetting characteristics of the subject epothilones and analogs thereof, the initial solution may be prepared using, initially, a greater concentration of alcohol to water, for example, a mixture of about 60% v/v, or from about 60% to about 95% v/v, tertiary butanol and water. Once the solution is made, the requisite amount of water or tertiary-butanol-water mixture can be added to achieve the desired final concentration for lyophilization as stated above.

Advantageously, as previously described in the above-cited US patent applications, the solution for lyophilization is prepared at a temperature below ambient temperature, for example, from about 5° C. to about 15° C., or at 5° C., to minimize degradation of the subject epothilone analogs. Both the process of forming the solution and subsequent lyophilization advantageously can be carried out in vessels such that the epothilones or analogs thereof are protected from exposure to light. It is also beneficial to perform the lyophilization in comparatively small batches so that the epothilones or analogs-thereof are exposed to an aqueous medium for a minimum amount of time.

The lyophilization preferably is performed in two stages, wherein the primary drying stage of lyophilization of the solution formed as described above is carried out at temperatures from about −10° C. to about −40° C., for example, about −25° C., under high vacuum, i.e., from about 50 millitorr to about 300 millitorr, for example, about 200 millitorr, for an extended period, i.e., from about 24 hours to about 100 hours, for example, about 48 hours. Lyophilization in this temperature range produces an amorphous product which is desirable for an intravenous preparation. Those of ordinary skill in the art will appreciate that conventional procedures, such as powder X-ray diffraction, can be utilized to confirm the amorphous nature of the lyophilized product.

A secondary drying stage preferably is carried out to remove residual solvents. This secondary drying stage is preferably carried out at temperatures of from about 10° C. to about 30° C., for example, about 25° C., under high vacuum, i.e., from about 50 millitorr to about 300 millitorr, for example, about 150 millitorr for an extended period, i.e., from about 24 hours to about 96 hours, for example, about 48 hours.

In performing the lyophilization, in a preferred embodiment, excipients commonly utilized for such purposes, such as lactose, mannitol, dextran, and the like, are not included. Certain of these excipients may have a negative effect on the stability of the lyophilized product (lyophile). Hence, the epothilone analogs formulated in accordance with the present invention preferably are lyophilized neat, i.e., without any excipient. However, it is contemplated that the invention herein may be carried out with use of such excipients which will be known to one skilled in the field.

During the lyophilization process, applicants discovered that the successful drying of the product can be achieved by carefully controlling shelf fluid temperature and chamber pressure. Due to the high vapor pressure of tertiary butyl alcohol, the high vacuum conditions that exist during lyophilization can cause portions of the dry cake to break off and be carried out of the vial. It was found that this loss of product from the vial can be prevented by controlling the rate of sublimation. By carefully controlling shelf fluid temperature and chamber pressure, the rate of sublimation can be reduced so that loss of product is prevented. During the primary drying phase of the lyophilization cycle, chamber pressure is advantageously controlled in the range of about 200 to about 300 microns, more preferably in the range of about 225 to about 275 microns, and most preferably at about 250 microns, and shelf fluid temperature is advantageously controlled in the range of about −35° C. to about −25° C., more preferably in the range of about −32° C. to about −28° C., and most preferably at about −30° C. Under these conditions, the rate of sublimation is reduced and loss of product is reduced or does not occur.

According to one embodiment of the invention, it is contemplated that the epothilones or analogs thereof and the solution vehicle (or reconstitution vehicle, in the case of lyophilized compound) are each contained in separate vials and sold as a two-vial kit. Advantageously, these vials are light-protected. The infusion fluids or diluents are generally available in clinical facilities and may or may not be sold in the kit. It is, however, within the scope of the present invention to package the subject epothilones or analogs with a third vial containing sufficient infusion fluid or diluent to prepare the final concentration for administration.

Varying potencies (such as 0.5 to 100 mg/vial) of the lyophilized epothilones or analogs thereof, maybe packaged in vials. For example, vials containing 15 mg/vial, 20 mg/vial, or 30 mg/vial of an epothilone analog of formula I or II may be produced. When the solution or reconstitution vehicle is sold in a kit with at least one vial of epothilone or analog thereof, sufficient amount of the reconstitution vehicle may be provided to form a solution having a concentration of about 1 mg/mL to about 10 mg/mL of the epothilone or analog thereof, more preferably a concentration of about 1 mg/mL to 4 mg/mL. For example, vials containing the reconstitution vehicle may be provided with varying amounts of reconstitution vehicle, such as 5.5 mL/vial, 8 mL/vial or 16.5 mL/vial. The lyophilized compound is dissolved in the reconstitution vehicle, and then the resulting solution is further diluted in a suitable infusion fluid (or diluent) prior to injection into a patient. Such infusion fluids or diluents are well known to those of ordinary skill in the art. Upon addition of the diluent, the final concentration for administration could, for example, contain from about 0.1 mg/mL to about 0.9 mg/mL, such as from about 0.2 mg/mL to about 0.6 mg/mL, of the epothilones or analogs thereof, of formula I or II. This formulation has a pH of from about 6 to about 10 and exhibits significantly diminished acid-induced hydrolysis of the epoxide ring.

EXAMPLES

Example 1

[1S-[1R*,3R*(E),7R*,10S*,11R*,12R*,16S*]]-7,11-Dihydroxy-8,8,10,12,16-pentamethyl-3-[1-methyl-2-(2-methyl-4-thiazolyl)ethenyl]-4-aza-17-oxabicyclo[14.0]heptadecane-5,9-dione, 4.04 g, was wetted/partially dissolved with 500 mL of a 4:1 mixture of tertiary butanol and Water for Injection USP which had been pre-cooled to 5° C. Once the drug powder had become completely wetted, dissolution was completed by the addition of 300 mL Water for Injection, thereby making the final solution a 1:1 mixture. The dissolution was carried out under protection from light.

The solution formed above was promptly lyophilized in a Virtis GENESIS lyophilizer at −30° C. under light protected conditions over a period of about 100 hours. The resultant lyophilized product (lyophile) was then further dried at 25° C. under high vacuum for about 35 hours. No detectable degradation of the drug was observed during these procedures. The lyophile was packaged under sterile conditions into 15 mL vials, each containing 20 mg of drug and standard excess to allow for vial/needle/syringe loss.

The epothilone lyophile was reconstituted in reconstitution vehicle. The reconstitution vehicle was prepared with Dehydrated Alcohol USP, nonionic surfactant such as a polyethoxylated castor oil surfactant (available from GAF Corp., Mount Olive, N.J., under the tradename CREMOPHOR EL®), Sodium Lactate Solution, USP and Sodium Hydroxide Solution (such as a 1N or 2N Sodium Hydroxide solution). Sufficient amount of the reconstitution vehicle was provided to form a solution having a concentration of about 1 mg/mL to about 10 mg/mL of the epothilone analog. The reconstituted epothilone was further diluted in 0.9% Sodium Chloride Injection or 5% Dextrose Injection to a final concentration of about 0.2 mg/mL to about 0.6 mg/mL.

Example 2

The reconstitution vehicle was prepared as follows. The total amount of Dehydrated Alcohol required for the batch was calculated, and then 90% of the total required amount of Dehydrated Alcohol was added to a batch tank. With constant stirring, sufficient Sodium Lactate Solution (USP) was added so that the concentration of sodium lactate in the final formulation would be approximately 15 mg/mL. Next, cleaned CREMOPHOR EL® brand of polyethoxylated castor oil surfactant was added and the batch was mixed for a minimum of 30 minutes. Sodium Hydroxide Solution (2N) was then added to adjust batch pH to 8.2 to 8.6. Then the remaining amount of Dehydrated Alcohol was added and mixed for a minimum of 30 minutes. The solution was then aseptically filtered through a 0.22 μm membrane filter into a sterilized container. The solution was next filled into sterilized vials. Finally, these vials containing the reconstitution vehicle were fitted aseptically with stoppers and then sealed.

Example of the quantitative composition of the reconstitution vehicle are shown in Table 1 below.

TABLE 1

Quantitative Composition of the Reconstitution Vehicle

| Ingredients | Amount per 100 mL |
|---|---|
| CREMOPHOR EL ® brand of polyethoxylated castor oil | 49.0 mL |
| Dehydrated Alcohol, USP | 49.0 mL |
| Sodium Lactate Solution, USP | 1.91 mL |
| 2N Sodium Hydroxide Solution | Qs to pH 8.4 |

What is claimed is:

1. A pharmaceutical formulation for parenteral administration as a solution of an epothilone analog to a patient, the epothilone analog having the formula:

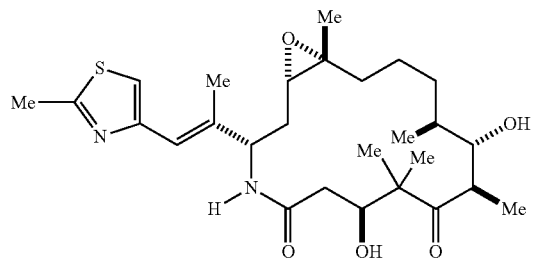

wherein the formulation comprises 1) an infusion fluid selected from the group consisting of saline and dextrose, and excluding Lactated Ringer's Solution, having an infusion fluid pH, wherein the epothilone analog has a pH of maximum stability different from the infusion fluid pH to define a pH differential; and 2) a pharmaceutical preparation comprising said epothilones analog, and a reconstitution vehicle comprising (a) a nonionic surfactant, (b) a solvent which comprises an alcohol, (c) a buffer, and (d) a pH-adjusting ingredient, wherein the buffer and the pH-adjusting ingredient are selected so that when the pharmaceutical preparation is mixed with the infusion fluid to provide the solution formulation for parenteral administration said formulation has a pH within the range from 6 to 9, wherein the buffer is sodium lactate and is present in the pharmaceutical formulation in a concentration between about 10 to about 20 mg/mL, wherein the pH-adjusting ingredient is a base, sodium hydroxide and is present at a concentration of from about 0.01 mg/mL to about 1 mg/mL, and wherein the compound of formula above is present in the formulation for administration in a concentration between about 0.1 mg/mL and about 0.9 mg/mL, said formulation for parenteral administration being free of Lactated Ringer's Solution and having an enhanced stability of about 25% or greater determined over a period for 0 to 24 hours as compared to a formulation having the same ingredients except without buffer and pH-adjusting ingredient.

2. The pharmaceutical formulation of claim 1 wherein the pH-adjusting ingredient is a base, and the pharmaceutical formulation consists essentially of the epothilone analog compound, buffer, the base, the alcohol, and a nonionic surfactant.

3. The pharmaceutical formulation of claim 1 wherein the infusion fluid is saline, and the pharmaceutical formulation has a pH in the range from 6 to 9.

4. The pharmaceutical formulation of claim 1 wherein the infusion fluid of the formulation for administration is dextrose, the pharmaceutical formulation has a pH in the range from 6 to 9.

5. A process for parenterally administering to a patient an epothilone analog compound, with an infusion fluid which is dextrose or saline and excludes Lactated Ringer's Solution having an infusion fluid pH, the compound having the formula,

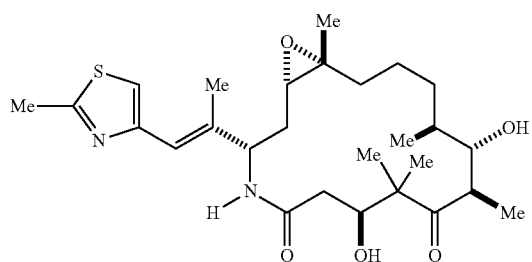

wherein the compound has a pH of maximum stability that is different from the infusion fluid pH, to define a pH differential;

the process comprising dissolving the compound in a first, solution or reconstitution vehicle to provide an epothilone solution, wherein the solution vehicle includes a solvent which comprises an alcohol, a nonionic surfactant, at least one buffer and at least one pH-adjusting ingredient, the buffer and pH-adjusting ingredient being selected so that, when the epothilone solution is mixed with the infusion fluid which is selected from the dextrose or saline to provide the formulation in the form of a solution for parenteral administration, the difference between the pH of the formulation for parenteral administration and the pH of maximum stability for the compound is less than the pH differential, said formulation for parenteral administration having a pH within the range from 6 to 9, and wherein the buffer is sodium lactate and is present in the pharmaceutical formulation in a concentration between about 10 to about 20 mg/mL, wherein the pH-adjusting ingredient is a base, sodium hydroxide and is present at a concentration of from about 0.01 mg/mL to about 1 mg/mL, and wherein the compound of formula above is present in the formulation for administration in a concentration between about 0.1 mg/mL and about 0.9 mg/mL, said formulation in the form of a solution for parenteral administration, free of Lactated Ringer's Solution, having an enhanced stability of about 25% or greater determined over a period for 0 to 24 hours as compared to a formulation having the same ingredients except without buffer and pH-adjusting ingredient.

6. The process of claim 5, wherein the solution vehicle is prepared to achieve a pH in the range of about 6 to about 9.

7. A kit for preparing a formulation for parenteral administration as defined in claim 1, the formulation for parenteral administration comprising:

i) an infusion fluid having an infusion fluid pH which infusion fluid is selected from the group consisting essentially of saline and dextrose and free of Lactated Ringer's Solution; and ii) an epothilone analog compound of the formula:

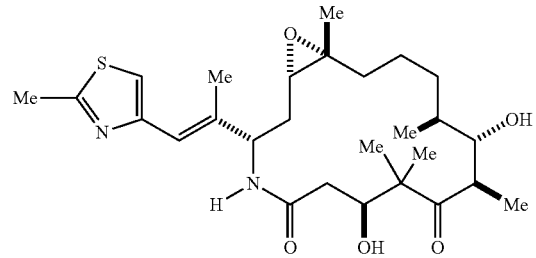

wherein the compound has a pH of maximum stability different from the infusion fluid pH to define a pH differential; the kit comprising: in a first vial, the epothilone analog compound; and in a second vial, a pharmaceutical preparation comprising a reconstitution vehicle comprising a nonionic surfactant, a solvent comprising an alcohol, a buffer, and a pH-adjusting ingredient, wherein the buffer and pH-adjusting ingredient are selected so that when the epothilone analog compound, buffer and pH-adjusting ingredient are added to the infusion fluid to provide the formulation for administration the formulation has a pH within the range from 6 to 9, and wherein the buffer is sodium lactate and is present in the pharmaceutical formulation in a concentration between about 10 to about 20 mg/mL, wherein the pH-adjusting ingredient is a base, sodium hydroxide and is present at a concentration of from about 0.01 mg/mL to about 1 mg/mL, and wherein the compound of formula above is present in the formulation for administration in a concentration between about 0.1 mg/mL and about 0.9 mg/mL, said formulation for parenteral administration, being free of Lactated Ringer's Solution, having an enhanced stability of about 25% or greater determined over a period for 0 to 24 hours as compared to a formulation having the same ingredients except without buffer and pH-adjusting ingredient.

8. The kit of claim 7, wherein the epothilone analog compound in the first vial is lyophilized, and the pharmaceutical preparation in the second vial is a reconstitution vehicle.

* * * * *

UNITED STATES PATENT AND TRADEMARK OFFICE
CERTIFICATE OF CORRECTION

PATENT NO.       : 8,871,227 B2
APPLICATION NO.  : 12/557822
DATED            : October 28, 2014
INVENTOR(S)      : Thomas A. Haby et al.

It is certified that error appears in the above-identified patent and that said Letters Patent is hereby corrected as shown below:

In the Claims:

Claim 1:

Column 16, line 31, change "9" to -- 9, and --.

Signed and Sealed this
Thirty-first Day of March, 2015

Michelle K. Lee
*Director of the United States Patent and Trademark Office*